(12) United States Patent
Shigeru et al.

(10) Patent No.: US 6,509,057 B2
(45) Date of Patent: Jan. 21, 2003

(54) ANTIBACTERIAL, ANTIFUNGAL OR ANTIALGAL ARTICLE AND PROCESS FOR PRODUCING SAME

(75) Inventors: Keijiro Shigeru, Funabashi (JP); Takako Yazawa, Funabashi (JP); Yoshitomo Inoue, Funabashi (JP); Yasuyuki Kurino, Funabashi (JP)

(73) Assignee: Sumitomo Osaka Cement, Co., Ltd. (JP)

( * ) Notice: Subject to any disclaimer, the term of this patent is extended or adjusted under 35 U.S.C. 154(b) by 0 days.

(21) Appl. No.: 09/804,703

(22) Filed: Mar. 13, 2001

(65) Prior Publication Data

US 2002/0001604 A1 Jan. 3, 2002

Related U.S. Application Data

(62) Division of application No. 09/053,596, filed on Apr. 1, 1998, now abandoned.

(51) Int. Cl.[7] .......................... A61K 6/00; A01N 25/00; B22F 3/00; B05D 1/16

(52) U.S. Cl. .......................... 427/11; 424/401; 424/405; 428/546; 427/464

(58) Field of Search .......................... 428/546; 424/401; 427/464

(56) References Cited

U.S. PATENT DOCUMENTS 6,180,162 B1 * 1/2001 Shigeru et al. ............... 427/11

FOREIGN PATENT DOCUMENTS

| JP | 07228999 | * | 8/1995 |
| JP | 08059406 | * | 3/1996 |

* cited by examiner

*Primary Examiner*—Jose' G. Dees
*Assistant Examiner*—Robert M DeWitty
(74) *Attorney, Agent, or Firm*—Paul & Paul

(57) ABSTRACT

An antibacterial, antifungal or antialgal article includes an antibacterial, antifungal or antialgal component, for example, silver and copper, an alloy thereof or a compound thereof diffused from a surface into the inside of the surface portion of an article, for example, a metal, glass or ceramic article.

3 Claims, 1 Drawing Sheet

ANTIBACTERIAL, ANTIFUNGAL OR ANTIALGAL ARTICLE AND PROCESS FOR PRODUCING SAME

This application is a division of application Ser. No. 09/053,596, filed Apr. 1, 1998, now abandoned.

BACKGROUND OF THE INVENTION

1. Field of the Invention

The present invention relates to an article imparted with an antibacterial, antifungal or antialgal property, more preferably an antibacterial, antifungal or antialgal article in which an antibacterial, antifungal or antialgal property is imparted to an article comprising a metallic material, for example, stainless steel or aluminum, etc., a glass material or a ceramic material, for example, pottery, which is often utilized in industry and at home, and a process for producing same.

2. Description of the Related Art

The processes for imparting an antibacterial, antifungal or antialgal property to an article formed from metal, glass and ceramic materials, etc. are divided broadly or two categories.

In one category, an antibacterial, antifungal or antialgal agent is directly knead-mixed into a material. In this case, when a metal, glass or ceramic material is used, since the material is formed at a high forming temperature, an inorganic antibacterial, antifungal or antialgal agent containing a silver and copper-containing antibacterial agent is used.

The other category is a coating process in which a coating layer comprising an antibacterial, antifungal or antialgal agent is formed on a surface of an article. For example, a coating liquid prepared by dispersing an antibacterial, antifungal or antialgal agent together with a resin vehicle in a solvent is coated on the article, or a glaze containing a glaze component added with an antibacterial, antifungal or antialgal agent is applied. In the former, both organic and inorganic antibacterial, antifungal or antialgal agents can be used and, in the later case, an inorganic antibacterial, antifungal or antialgal agent is used.

However, the conventional process for imparting an antibacterial property, for example, a knead-mixing process, is disadvantageous in that since the forming temperature for the metal, glass and ceramic materials is high, when an inorganic antibacterial, antifungal or antialgal agent having a poor heat resistance is used, a satisfactory antibacterial property is difficult to exhibit and, even when a satisfactory antibacterial, antifungal or antialgal property is attained, a portion of the antibacterial, antifungal or antialgal agent is distributed even in the deep inside portion of the article and does not impart an effective action to the bacteria cohered to the surface of the art, and thus an economical disadvantage occurs. (Refer to FIG. 1)

Also, the conventional coating method does not have the economical disadvantage of the knead-mixing method, because a coating layer having an antibacterial, antifungal or antialgal property is newly formed on a surface of a previously formed article. However, this method is disadvantageous in that the binder (resin vehicle or glaze component) in the coating layer is worn by abrasion within a relatively short term; the surface properties (for example, color and physical properties) of the article are significantly changed by the formation of the coating layer, and when a glaze containing an antibacterial, antifungal or antialgal agent added to a glaze component is coated and baked, the baking temperature is 800° C. or more and thus the antibacterial, antifungal or antialgal properties are degraded. (Refer to FIG. 2)

SUMMARY OF THE INVENTION

The present invention was effected in consideration of the above-mentioned problems of the prior arts and an object of the present invention is to provide an antibacterial, antifungal or antialgal article containing an antibacterial, antifungal or antialgal agent concentratedly distributing in a surface portion of the article, of which article the antibacterial, antifungal or antialgal property is not exhausted within a short term by abrasion, etc., and is not degraded by heat-treatment and, on the surface properties of which article, a significant change due to the formation of a coating layer does not occur, and a process for producing the same.

The object of the present invention can be attained by an antibacterial, antifungal or antialgal article of the present invention which is characterized in that an antibacterial, antifungal or antialgal component has been diffused from a surface of the article into the inside of the surface portion of the article.

In the antibacterial, antifungal or antialgal article of the present invention, the antibacterial, antifungal or antialgal component preferably comprises at least one member selected from the group consisting of silver, copper, silver-copper alloys, organic silver compounds, organic copper compounds, silver chloride, silver sulfide, silver oxide, silver sulfate, cuprous chloride and cupric chloride and cuprous sulfide.

DESCRIPTION OF THE PREFERRED EMBODIMENTS

Figure 1:
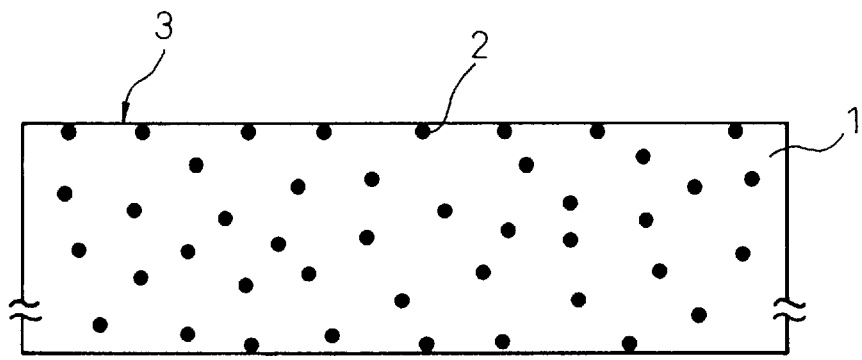
FIG. 1 is an explanatory cross-sectional view of a conventional article imparted with an antibacterial, antifungal or antialgal property, in which article an antibacterial, antifungal or antialgal component is distributed by a knead-mixing process.

In FIG. 1, an antibacterial, antifungal or antialgal article produced by a conventional knead-mixing method is shown. In the article 1 of FIG. 1, fine particles 2 of an antibacterial, antifungal or antialgal component are evenly distributed throughout the article 1, and some of the particles are located at the surface 3 of the article 1.

Figure 2:
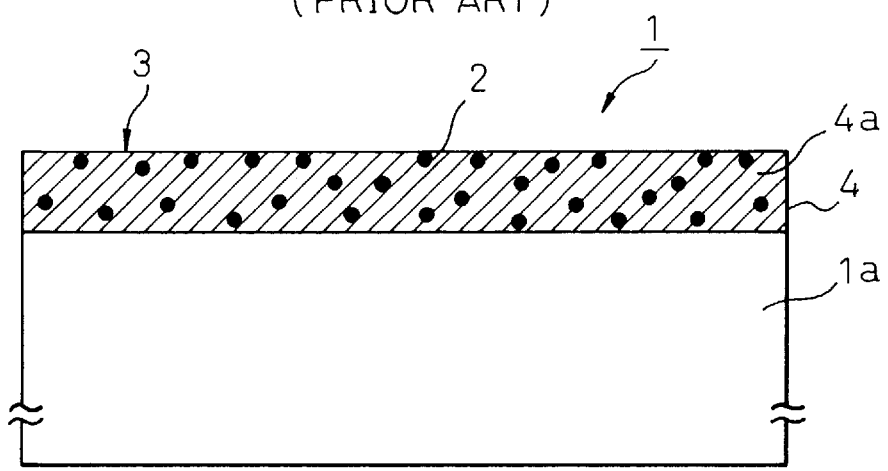
FIG. 2 is an explanatory cross-sectional view of a conventional article imparted with an antibacterial, antifungal or antialgal property, in which article an antibacterial, antifungal or antialgal component is distributed by a coating process.

In FIG. 2, an antibacterial, antifungal or antialgal article produced by a conventional coating method is shown.

In the article 1 of FIG. 2, a substrate 1a is coated by a coating layer 4 comprising a binder 4a and fine particles 2 of an antibacterial, antifungal or antialgal component dispersed in the binder 4a, and some of the particles 2 are located in the surface 3 of the coating layer.

Figure 3:
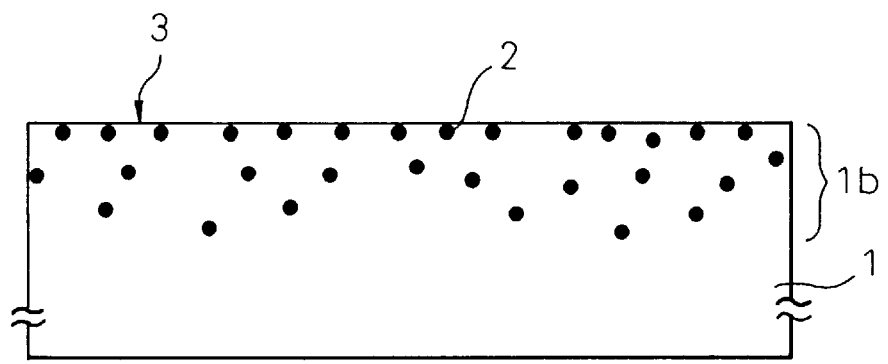
FIG. 3 is an explanatory cross-sectional view of an antibacterial, antifungal or antialgal article in which an antibacterial, antifungal or antialgal component is distributed in accordance with the process of the present invention.

In FIG. 3, an antibacterial, antifungal or antialgal article in accordance with the present invention is shown. In FIG. 3, fine particles 2 of an antibacterial, antifungal or antialgal component are located only in a surface portion 1b of the article 1.

The inventors of the present invention found that the problems of the prior arts can be solved by coating an antibacterial, antifungal or antialgal component on a surface of an article, and heating the coated article at a relatively low temperature, and have completed the present invention based on the above-mentioned finding.

In the present invention, an antibacterial, antifungal or antialgal component is directly diffused from a surface of an article into the inside of a surface portion of the article. Namely, the antibacterial, antifungal or antialgal component is distributed in a large amount in a portion of the article close to the surface of the article. However, in the middle portion of the article, substantially no antibacterial, antifungal or antialgal component is distributed. Also, on the surface of the article, substantially no binder component and no fuse-adhered film of the antibacterial, antifungal or antialgal component are distributed.

Accordingly, even when the surface of the article is slightly worn, the antibacterial, antifungal or antialgal property of the article is not lost and, since the surface of the article is not coated with another material, the surface properties, for example the color, of the article are not greatly changed. (Refer to FIG. 3).

Practical embodiments of the present invention will be explained below.

To diffuse an antibacterial, antifungal or antialgal component into the inside of a surface portion of an article, a fine particle dispersion or solution of the antibacterial, antifungal or antialgal component (which will be referred to as a coating liquid hereinafter) is coated on a desired surface of the article, and the coated article is heated, to cause the antibacterial, antifungal or antialgal component to diffuse from the article surface to the inside of the surface portion of the article.

The articles to be subjected to the antibacterial, antifungal or antialgal treatment must be resistive to heat-treatment at, for example, a temperature of at least 200° C., and can be selected from, for example, metal, glass and ceramic materials, etc. These articles do not need to contain pores connected to the outside space and thus may be dense article substantially free from pores.

The surfaces of these articles to be subjected to the antibacterial, antifungal or antialgal treatment are fully washed before applying the coating liquid, to remove stains from the surfaces.

As an antibacterial, antifungal or antialgal component, a material having a high heat resistance, exhibiting an oligo-dynamic effect and containing no organic or inorganic binder component (for example, a glaze component) which will remain after the heat treatment, can be used.

The antibacterial, antifungal or antialgal component preferably comprises one or two or more members selected from the group consisting of silver, copper the group consisting of, silver-copper alloys, organic silver compounds, organic copper compounds, silver chloride, silver sulfide, silver oxide, silver sulfate, cuprous chloride, cupric chloride, cuprous sulfide, cupric sulfide, cuprous oxide, cupric oxide, cuprous sulfate and cupric sulfate in view of the facts that they can easily diffuse into the inside of the surface portion of the article, have a high safety, and exhibit no influence on the surface properties, for example the color, of the article.

The coating liquid is prepared by dispersing or dissolving fine particles of the antibacterial, antifungal or antialgal component in water or an organic solvent, and is preferably mixed with a surfactant to enhance the wetting of the article surfaces.

The coating procedure of the coating liquid is not limited to specific procedures and may be carried out by a brushing, dipping or spraying method.

In the coating liquid, the antibacterial, antifungal or antialgal component is preferably in a concentration of 0.01 to 10% by weight. If the concentration is lower than 0.01%, the resultant antibacterial, antifungal or antialgal property may be insufficient and if the concentration is more than 10%, a fuse-cohered film of the antibacterial, antifungal or antialgal component or a residual stain may be formed on the resultant article surface, or a residual stain may remain on the surface.

The fine antibacterial, antifungal or antialgal particles preferably have a particle size of 10 $\mu$m or less, more preferably 0.1 $\mu$m or less in which the particles are in the state of colloidal particles. When the colloidal antibacterial, antifungal or antialgal particles are used, the diffusion of the particles into the inside of the surface portion of the article occurs easily.

The heat treatment is carried out for example, at a temperature of 200° C. or more. The suitable heat treatment temperature is variable in response to the type of material for the article and the type of the antibacterial, antifungal or antialgal component.

Namely, the higher the heat treatment temperature, the higher the diffusion rate. Therefore, the diffusion temperature is preferably 200° C. or more. (When the diffusion temperature is lower than 200° C., an easily diffusible antibacterial, antifungal or antialgal component such as silver or copper cannot diffuse). The heat treatment temperature is established at a level at which the article is not affected, for example, the color of the article is not changed and the mechanical strength of the article is not decreased, and the activity of the antibacterial, antifungal or antialgal component is not degraded.

Not to affect the article, the heat treatment temperature must satisfy at least one of the conditions, for example, described below:

① when the article is a sintered article, the heat treatment temperature is lower than the sintering temperature, ② when the article is not a sintered article, the heat treatment temperature is lower than the melting temperature of the article, and ③ when a coating layer (a glaze or porcelain enamel layer) is previously formed on the surface of the article, the heat treatment temperature is lower than the melting temperature of the coating layer.

If the heat treatment is carried out at a temperature above the above-mentioned temperatures, the accuracy in dimensions, the mechanical strength and the surface color of the article may be affected.

Also, even when the heat treatment temperature is lower than the above-mentioned temperature, the heat treatment temperature should not fall within the temperature range in which the physical properties of the article are degraded, for example, in the case of a stainless steel, of 400 to 800° C.

The suitable heat treatment temperature at which the performance of the antibacterial, antifungal or antialgal component does not decrease is established in consideration of the type of the antibacterial, antifungal or antialgal component used and is usually 800° C. or less.

The heat treatment time is established in consideration of the type of the article to be treated, the type of the antibacterial, antifungal or antialgal component, and the diffusion depth of the antibacterial, antifungal or antialgal component.

Usually, it is about 10 minutes to 100 hours. For example, in the case of a pottery which is a typical ceramic material, the heat treatment can be carried out at a temperature of about 300° C. In this case, a heat treatment time of about 10 minutes is long enough.

In the case of a glass plate which is a common glass material, the heat treatment is preferably carried out at a temperature of about 400 to 500° C. At this temperature, a heat treatment should be carried out for a time of about 10 minutes.

In the case of an aluminum which is a metal material, the heat treatment is carried out at a temperature of about 500° C. At the temperature of about 500° C., the heat treatment should be carried out for a time of about 30 minutes to one hour.

In the case of a stainless steel which is a metal material, the mechanical strength of the stainless steel article reduces at a temperature in the range of from 400 to 800° C. Therefore, the heat treatment must be carried out at a temperature above or below the above-mentioned temperature range. At a temperature of 380° C., the heat treatment must be carried out for a time of about one hour. Also, at a temperature of 820° C., the heat treatment can be completed within a few tens of minutes.

The coating-heat treatment can be utilized as a heat treatment step for the article during the production process of the article. For example, when a metal material or a glass material is used for the article, a heat treatment, for example, an annealing and/or a tempering treatment is applied to the material. In this case, when the coating liquid is applied to the material before the heat treatment step, the annealing and/or tempering step can serve as an antibacterial, antifungal or antialgal property-imparting step.

There is no limitation to the type of the heat treatment atmosphere. However, if the article is affected to a certain extent, the atmosphere is selected from, for example, non-oxidative atmospheres.

In the heat treatment procedure, no pressurization is necessary. However, when a pressure is applied, it is possible to shorten the heat treatment time and to increase the diffusion depth.

After the heat treatment is completed, a residual non-diffused component may form a fuse-cohered film on the article surface, or impurities may remain on the article surface. In this case, the fuse-cohered film and residual impurities can be easily removed by washing with an acid or by grinding.

Since the antibacterial, antifungal or antialgal component has been diffused into the inside of the surface portion of the article, even when the non-diffused component is removed from the surface, the antibacterial, antifungal or antialgal property is not lost or degraded, and the resultant article exhibits a strong antibacterial, antifungal or antialgal property.

With respect to the antibacterial, antifungal or antialgal property, it is considered that a portion of the antibacterial, antifungal or antialgal component exposing on the surface of the article can exhibit the antibacterial, antifungal or antialgal performance. Also, even when the surface of the article is worn or corroded, a portion of the antibacterial, antifungal or antialgal component is exposed on the newly formed surface of the article and thus the antibacterial, antifungal or antialgal performance of the article is not degraded.

In any of the above-mentioned cases, when an antibacterial, antifungal or antialgal component typically represented by silver or copper is coated on a surface of an article such as a metal, glass or ceramic article and heat-treated, the antibacterial, antifungal or antialgal component diffuses into the inside of the article and the surface of the article exhibits a good antibacterial, antifungal or antialgal performance.

As shown in FIG. 3, in an embodiment of the present invention, the antibacterial, antifungal or antialgal component is distributed on or close to the surface of the article, while using no binder component, and thus an economical disadvantage which occurs in the conventional knead-mixing method, a reduction in the antibacterial, antifungal or antialgal property, a peeling off and separation of the coated layer, and a change in the surface properties, which occur in the conventional coating method, do not occur.

Also, since the production process of the antibacterial, antifungal or antialgal article basically comprises only the coating and heat treating steps, and restriction in article-formation is small.

Therefore, even in a dense article, for example, a dense ceramic, a metal or a glass article, having substantially no pores connected to the outside space of the article, the antibacterial, antifungal or antialgal component can diffuse into the inside of the article through boundaries between particles and lattices and thus the antibacterial, antifungal or antialgal component can reach the inside of the surface portion of the article. When the fine particles of the antibacterial, antifungal or antialgal component are coated on the surface of the dense article, the use of a dispersion containing the fine particles or a solution of the fine particles allows the component to easily and uniformly diffuse into the dense article.

EXAMPLES

The present invention will be further explained in detail by the following examples which are merely representative and do not restrict the scope of the present invention in any way.

In the examples, each of the articles was fully cleaned with an aqueous soap solution before coating a coating liquid thereon.

Example 1

An aqueous silver colloid dispersion having a silver colloid concentration of 1% by weight, and an average particle size of 0.08 $\mu$m was prepared by a conventional method, and coated on a dense soda-lime glass plate having a density of about 100% and a glass-softening temperature of 520° C. by a dipping method, with a dry coating amount of 5 g/m$^2$. After drying, the dried coating layer was heat-treated in ambient atmosphere at a temperature of 500° C. for 30 minutes.

The resultant glass plate is transparent as before the treatment, and no discoloration was found on the treated glass plate.

Example 2

Copper particles were pulverized in turpentine oil to prepare a copper dispersion having a copper concentration of 1% by weight and an average particle size of 1 $\mu$m. The copper dispersion was coated in a dry coating amount of 1 g/m$^2$, on a surface of pottery (glazed with a glaze having a melting temperature of 920° C. and sintered at a temperature of 1200° C.), and then heat-treated in ambient atmosphere at a temperature of 300° C. for 10 minutes.

The obtained pottery had a slightly bluish color. When pickled with an aqueous solution of 10% by weight of nitric acid, the resultant pickled pottery exhibited the same appearance as the original.

Example 3

Silver citrate was pulverized in water to prepare a silver citrate dispersion having a silver citrate concentration of 0.5% by weight and an average particle size of 0.5 $\mu$m. The silver citrate dispersion was coated in a dry coating amount of 10 g/m$^2$ on a surface of an aluminum plate having a density of 98.8% and a melting temperature of 640° C., by a spray method, dried and then heat treated in ambient atmosphere at a temperature of 500° C. for 30 minutes.

The obtained aluminum plate had substantially same appearance as before the treatment.

Example 4

Copper sulfate was pulverized in turpentine oil to prepare a copper sulfate dispersion having a copper sulfate concentration of 2% by weight and an average particle size of 2 $\mu$m. The copper sulfate dispersion was coated in a dry coating amount of 0.5 g/m$^2$ on a surface of a dense stainless steel plate produced by an ingot method and having a density of 99.5% and a melting temperature of 1400° C. by a spray method, and heat treated in a hydrogen gas atmosphere at a temperature of 400° C. for 20 minutes.

The resultant treated stainless steel surface was cohered with a small amount of copper-containing stain. After pickling with an aqueous solution of 10% by weight of nitric acid, the pickled plate had the same appearance as the original.

Comparative Examples 1 to 4

Comparative Examples 1 to 4 were carried out respectively by the same procedures as in Examples 1 to 4, except that no antibacterial, antifungal or antialgal treatment was applied.

Comparative Example 5

Fine copper particles having an average particle size of 1 $\mu$m were prepared by wash-removing the turpentine oil from the same copper dispersion as in Example 2 with ethyl alcohol. A glaze liquid containing the fine copper particles was coated on the same pottery as in Example 2 and the coated glaze liquid layer was heat treated at a temperature of 1200° C. in ambient atmosphere.

In the glaze layer formed on the surface of the pottery, the content of copper was 0.01 g/cm$^2$ which was the same as in Example 2.

The glazed pottery was subjected to an antibacterial, antifungal or antialgal property evaluation as shown below.

Evaluation of the products of the examples and comparative examples.

The antibacterial property of the samples of Examples 1 to 4 and Comparative Examples 1 to 5 was evaluated as follows.

On a surface of each of the samples of Examples 1 to 4 and comparative samples prepared in Comparative Examples 1 to 4 in which no antibacterial, antifungal or antialgal treatment was applied, and in Comparative Example 5, 0.1 ml of a liquid containing a bacterium selected from *staphylococcus aureus, bacillus subtilis,* colibacillus, *klebsiella pneumoniae,* salmonella, and *pseudomonas aeruginosa,* was placed and left to stand at a temperature of 37° C. for 24 hours and then the number of living bacteria was measured by an agar plate count method.

Also, a mold or alga were cultivated at a temperature of 27° C. for a predetermined time, and the ontogeny of the mold or alga was observed by naked eye.

The evaluation results are shown in Tables 1 and 2.

TABLE 1

| | Antibacterial property (cfu/ml) | | | | | | | |
|---|---|---|---|---|---|---|---|---|
| | *Staphylococcus aureus* | | *Bacillus subtilis* | | Colibacillus | | *Kiebsilla pneumoniae* | |
| Item Example No. | At the start | 24 hours after the start | At the start | 24 hours after the start | At the start | 24 hours after the start | At the start | 24 hours after the start |
| Example 1 | 1.8 × 10$^5$ | 10$^2$ >$^{(*)1}$ | 2.3 × 10$^5$ | 10$^2$ > | 4.1 × 10$^5$ | 10$^2$ > | 1.6 × 10$^5$ | 10$^2$ > |
| Comparative Example 1 | 1.8 × 10$^5$ | 1.7 × 10$^5$ | 2.3 × 10$^5$ | 2.3 × 10$^5$ | 4.1 × 10$^5$ | 3.6 × 10$^5$ | 1.6 × 10$^5$ | 1.6 × 10$^5$ |
| Example 2 | 1.8 × 10$^5$ | 10$^2$ > | 2.3 × 10$^5$ | 10$^2$ > | 4.1 × 10$^5$ | 10$^2$ > | 1.6 × 10$^5$ | 10$^2$ > |
| Comparative Example 2 | 1.8 × 10$^5$ | 1.4 × 10$^5$ | 2.3 × 10$^5$ | 2.2 × 10$^5$ | 4.1 × 10$^5$ | 3.7 × 10$^5$ | 1.6 × 10$^5$ | 1.2 × 10$^5$ |
| Example 3 | 1.8 × 10$^5$ | 10$^2$ > | 2.3 × 10$^5$ | 10$^2$ > | 4.1 × 10$^5$ | 10$^2$ > | 1.6 × 10$^5$ | 10$^2$ > |
| Comparative Example 3 | 1.8 × 10$^5$ | 1.1 × 10$^5$ | 2.3 × 10$^5$ | 1.7 × 10$^5$ | 4.1 × 10$^5$ | 3.4 × 10$^5$ | 1.6 × 10$^5$ | 1.2 × 10$^5$ |
| Example 4 | 1.8 × 10$^5$ | 10$^2$ > | 2.3 × 10$^5$ | 10$^2$ > | 4.1 × 10$^5$ | 10$^2$ > | 1.6 × 10$^5$ | 10$^2$ > |
| Comparative Example 4 | 1.8 × 10$^5$ | 1.2 × 10$^5$ | 2.3 × 10$^5$ | 1.7 × 10$^5$ | 4.1 × 10$^5$ | 3.2 × 10$^5$ | 1.6 × 10$^5$ | 1.3 × 10$^5$ |
| Comparative Example 5 | 1.8 × 10$^5$ | 1.0 × 10$^4$ | 2.3 × 10$^5$ | 2.9 × 10$^4$ | 4.1 × 10$^5$ | 3.7 × 10$^4$ | 1.6 × 10$^5$ | 8.5 × 10$^4$ |

Note:
10$^2$ > . . . indicates that the number of bacteria per ml is less than 100.

TABLE 2

| Item Example No. | Antibacterial property (cfu/ml) | | | | Antifungal property (cfu/ml) | Antialgal property (cfu/ml) |
|---|---|---|---|---|---|---|
| | Salmonella | | Pseudomonas aeruginosa | | | |
| | At the start | 24 hours after the start | At the start | 24 hours after the start | 14 days after the start | 28 days after the start |
| Example 1 | $3.9 \times 10^5$ | $10^2 >$ | $1.9 \times 10^5$ | $10^2 >$ | 0 | 0 |
| Comparative Example 1 | $3.9 \times 10^5$ | $3.8 \times 10^5$ | $1.9 \times 10^5$ | $1.4 \times 10^5$ | 4 | 1 |
| Example 2 | $3.9 \times 10^5$ | $10^2 >$ | $1.9 \times 10^5$ | $10^2 >$ | 0 | 0 |
| Comparative Example 2 | $3.9 \times 10^5$ | $3.6 \times 10^5$ | $1.9 \times 10^5$ | $1.5 \times 10^5$ | 4 | 2 |
| Example 3 | $3.9 \times 10^5$ | $10^2 >$ | $1.9 \times 10^5$ | $10^2 >$ | 0 | 0 |
| Comparative Example 3 | $3.9 \times 10^5$ | $3.4 \times 10^5$ | $1.9 \times 10^5$ | $1.4 \times 10^5$ | 3 | 2 |
| Example 4 | $3.9 \times 10^5$ | $10^2 >$ | $1.9 \times 10^5$ | $10^2 >$ | 0 | 0 |
| Comparative Example 4 | $3.9 \times 10^5$ | $3.2 \times 10^5$ | $1.9 \times 10^5$ | $1.3 \times 10^5$ | 3 | 2 |
| Comparative Example 5 | $3.9 \times 10^5$ | $6.2 \times 10^4$ | $1.9 \times 10^5$ | $9.3 \times 10^4$ | 2 | 2 |

In Table 2, the antifungal or antialgal property was evaluated in accordance with the following evaluation classes.

| Class | Antifungal or antialgal property |
|---|---|
| 0 | No mold or alga generated |
| 1 | Very little amount of mold or alga generated |
| 2 | Moderate amount of mold or alga generated |
| 3 | Large amount of mold or alga generated |
| 4 | The surface of the sample were completely covered by the mold or alga. |

Table 1 shows that in all of Examples 1 to 4 wherein the antibacterial, antifungal or antialgal treatment was applied to the articles, the number of all types of the bacteria on the sample surfaces was reduced to less than 100 in the contact time of 24 hours, whereas in Comparative Examples wherein the antibacterial, antifungal or antialgal treatment of the present invention was not applied, the number of the bacteria on the surfaces of the samples was substantially not decreased.

On all of the sample surfaces treated by the antibacterial, antifungal or antialgal process of the present invention, no mold or alga was found, whereas on the non-treated sample surfaces, mold or alga was appeared.

Accordingly, it was confirmed that the articles of the present invention exhibit a satisfactory antibacterial, antifungal or antialgal property.

Also, it was confirmed that even after the antibacterial, antifungal or antialgal treatment-applied surface was pickled with an acid solution (as shown in Examples 2 and 4), the resultant pickled surface exhibited a high antibacterial, antifungal or antialgal property.

From the above-mentioned facts, it was also confirmed that the antibacterial, antifungal or antialgal component diffused into the inside of the surface portion of the article.

From the results shown in Tables 1 and 2, the article of Comparative Example 5 is poorer in the antibacterial, antifungal or antialgal property than that of Example 2.

In the antibacterial, antifungal or antialgal article of the present invention, an antibacterial, antifungal or antialgal component is diffused from the surface of an article into the inside of the surface portion of the article, and thus a high antibacterial, antifungal or antialgal property can be imparted to the article by utilizing a diffusion phenomenon substantially without forming a coating layer on the article surface. Therefore, the antibacterial, antifungal or antialgal property can be imparted to an article formed from a dense material such as a ceramic, glass or metal material.

Also, the process for producing the specific article of the present invention is easy and the heat-treatment can be carried out at a relatively low temperature, without deteriorating the performance of the antibacterial, antifungal or antialgal component. Also, since the resultant article per se exhibits a high antibacterial, antifungal or antialgal property, the characteristics of the article is not degraded and a degradation of the antibacterial, antifungal or antialgal performance of the article due to abrasion can be prevented. Also, an excessive consumption of the antibacterial, antifungal or antialgal component can be prevented.

The specific article of the present invention can be utilized as a cooking article, medical article, home-use article, building part, food container, or other machine part, which must be clean.

When the antibacterial, antifungal or antialgal component of the specific article of the present invention comprises at least one member selected from the group consisting of silver, copper, silver-copper alloys, organic silver compounds, organic copper compounds, silver chloride, silver sulfide, silver oxide, silver sulfate, cuprous chloride, cupric chloride, cuprous sulfide, cupric sulfide, cuprous oxide, cupric oxide, cuprous sulfate, and cupric sulfate, the antibacterial, antifungal or antialgal component exhibits a high diffusibility, a high safety in use, and an enhanced applicability, without affecting the surface properties, for example the color, of the article.

In the process of the present invention for producing an antibacterial, antifungal or antialgal article, a dispersion or solution of fine particles of an antibacterial, antifungal or antialgal component is coated on a desired surface of an article, and the dispersion or solution-coated article is heat-treated. In the heat treatment, the antibacterial, antifungal or antialgal component can easily diffuse into an article which may be a dense article having no pores connected to the outside space of the article, to enhance the antibacterial, antifungal or antialgal performance of the article, while preventing a decrease in the mechanical performance of the article, decreasing the consumption of the antibacterial, antifungal or antialgal component, enhancing the applicability of the article, decreasing the production cost, and enhancing the economic value of the article.

What is claimed is:

1. A process for producing an antibacterial, antifungal or antialgal metallic artide, comprising:

coating a dispersion consisting of fine particles of antibacterial, antifungal or antialgal metallic component comprising at least one member selected from the group consisting of metallic silver, metallic copper and silver copper alloys and free from binder, on a surface of a metallic article; and heating the coated metallic article at a temperature of 200° C. or more to cause the coated antibacterial, antifungal or antialgal metallic component to diffuse from the surface into the inside of the surface portion of the metallic article.

2. The process as claimed in claim 1, wherein the article comprises aluminum and the heating is carried out at a temperature of about 500° C. for 30 minutes to one hour.

3. The process as claimed in claim 1, wherein the article comprises a stainless steel, and the heating is carried out at a temperature of below 400° C. or above 800° C.

* * * * *